(12) United States Patent
Klosin

(10) Patent No.: US 6,248,914 B1
(45) Date of Patent: Jun. 19, 2001

(54) METALLOID SALT CATALYST/ACTIVATORS

(75) Inventor: Jerzy Klosin, Midland, MI (US)

(73) Assignee: The Dow Chemical Company, Midland, MI (US)

(*) Notice: Subject to any disclaimer, the term of this patent is extended or adjusted under 35 U.S.C. 154(b) by 0 days.

(21) Appl. No.: 09/289,335

(22) Filed: Apr. 9, 1999

Related U.S. Application Data

(60) Provisional application No. 60/096,946, filed on Aug. 18, 1998, and provisional application No. 60/104,369, filed on Oct. 15, 1998.

(51) Int. Cl.⁷ .............................. C07F 5/06; C07F 17/00; B01J 31/00

(52) U.S. Cl. ................................... 556/172; 556/1; 556/7; 556/17; 556/27; 556/28; 556/170; 556/187; 502/103; 502/117; 526/160; 526/443

(58) Field of Search ............................... 556/1, 7, 27, 28, 556/17, 172, 187, 170

(56) References Cited

U.S. PATENT DOCUMENTS

| | | | |
|---|---|---|---|
| 5,453,410 | 9/1995 | Kolthammer et al. | 502/155 |
| 5,602,269 | 2/1997 | Biagini et al. | 556/170 |
| 5,616,664 | 4/1997 | Timmers et al. | 526/127 |
| 5,624,878 | 4/1997 | Devore et al. | 502/152 |
| 5,721,185 | 2/1998 | La Pointe et al. | 502/117 |
| 5,777,120 | 7/1998 | Jordan et al. | 546/2 |

OTHER PUBLICATIONS

J. Am. Chem. Soc., Marks et al., 1996, 118, 12451–12452.
J. Am. Chem. Soc., Chen et al., 1997, 119, 2582–2583.
Organometallics, Jia et al., 1997, 16, 842–857.
J. Am. Chem. Soc., Coles et al., 1997, 119, 8125–8126.

(List continued on next page.)

Primary Examiner—Porfirio Nazario-Gonzalez

(57) ABSTRACT

A compound useful as a catalyst or as a cocatalyst in combination with a Group 3–10 metal for addition polymerizations corresponding to the formula:

$$[M'Q^1_2 L'_{l'}]^+ (Ar^f_3 MQ^2)^-$$

wherein:

M' is aluminum, gallium, or indium.

M is boron, aluminum, gallium or indium $Q^1$ is $C_{1-20}$ hydrocarbyl, optionally substituted with one or more groups which independently each occurrence are hydrocarbyloxy, hydrocarbylsiloxy, hydrocarbylsilylamino, di(hydrocarbylsilyl)amino, hydrocarbylamino, di(hydrocarbyl)amino, di(hydrocarbyl)phosphino, or hydrocarbylsulfido groups having from 1 to 20 atoms other than hydrogen, or, optionally, two or more $Q^1$ groups may be covalently linked with each other to form one or more fused rings or ring systems;

$Q^2$ is an alkyl group, optionally substituted with one or more cycloalkyl or aryl groups, said $Q^2$ having from 1 to 30 carbons;

L' is a monodentate or polydentate Lewis base;

l' is a number greater than zero indicating the number of Lewis base moieties, L', and $Ar^f$ independently each occurrence is an anionic ligand group of up to 30 atoms not counting hydrogen.

5 Claims, 2 Drawing Sheets

OTHER PUBLICATIONS

Schmidbaur et al., Isosteric Organometal Compounds. XII. Small Inorganic Rings. 1. Cycli Alumimosilazane Cation and its Gallium and Indium Ana–logs, Chem. Ber. vol. 102, No. 2, pp. 556–563, 1969 (no translation available).

Bruce et al., Cationic Alkyl Aluminum Ethylene Polymerization Catalysts Based on Monoanionic N, N, N–Pyridyliminoamide Ligands, Chem. Commun. No. 22, pp. 2523–2524, Nov. 10, 1998.

Radzewich et al., Reversible Ethylene Cycloaddition Reactions of Cationic Aluminum.Beta. —Diketiminate Complexes, J. Am. Chem. Soc., vol. 120, No. 36, pp. 9384–9385, Sep. 16, 1998.

Ihara et al., Cationic Aluminum Alkyl Complesex Incorporating Aminotroponimate Ligand, J. Am. Chem. Soc., vol. 120, No. 32, pp. 8277–8278, Aug. 19, 1998.

Jordan et al., Cationic Aluminum Alkyl Complexes. Transition–Metal–Free Olefin Polymerization Catalysts, Polym. Mater. Sci. Eng., vol. 80, pp. 418–419, Mar. 21, 1999.

METALLOID SALT CATALYST/ACTIVATORS

CROSS-REFERENCE TO RELATED APPLICATION

This application claims benefit of priority from provisional applications 60/096946, filed Aug. 18, 1998 and 60/104,369, filed Oct. 15, 1998.

BACKGROUND OF THE INVENTION

The present invention relates to compositions that are useful as catalyst activators for olefin polymerizations. More particularly the present invention relates to such compositions that are particularly adapted for use in the polymerization of unsaturated compounds having improved activation efficiency and performance. Such compositions are particularly advantageous for use in a polymerization process wherein catalyst, catalyst activator, and at least one polymerizable monomer are combined under polymerization conditions to form a polymeric product.

It is previously known in the art to activate Ziegler-Natta polymerization catalysts, particularly such catalysts comprising Group 3–10 metal complexes containing delocalized π-bonded ligand groups, by the use of an activator. Generally in the absence of such an activator compound, also referred to as a cocatalyst, little or no polymerization activity is observed.

A class of suitable activators are Lewis acids, especially alumoxanes, which are generally believed to be oligomeric or polymeric alkylaluminoxy compounds, including cyclic oligomers. Examples of alumoxanes (also known as aluminoxanes) include methylalumoxane (MAO) made by hydrolysis of trimethylaluminum as well as modified methylalumoxane (MMAO), wherein a portion of the trimethylaluminum is replaced by a higher alkyl aluminum compound such as triisobutylaluminum. MMAO advantageously is more soluble in aliphatic solvents than is MAO.

Generally alumoxanes contain, on average about 1.5 alkyl groups per aluminum atom, and are prepared by reaction of trialkylaluminum compounds or mixtures of compounds with water (Reddy et al, *Prog. Poly. Sci.*, 1995, 20, 309–367). The resulting product is in fact a mixture of various substituted aluminum compounds including especially, trialklyaluminum compounds. The amount of such free trialkylaluminum compound in the mixture generally varies from 1 to 50 percent by weight of the total product.

Although effective in forming an active olefin polymerization catalyst when combined with a variety of Group 3–10 metal complexes, especially Group 4 metal complexes, generally a large excess of alumoxane compared to metal complex, such as, molar ratios from 100:1 to 10,000:1, is required in order to produce adequate rates of polymerization. Unfortunately, the use of such large excesses of cocatalyst is expensive and also results in polymer having an elevated residual aluminum content. This latter factor may adversely affect polymer properties, especially clarity and dielectric constant.

A different type of activator compound is a Bronsted acid salt capable of transferring a proton to form a cationic derivative or other catalytically active derivative of such Group 3–10, metal complex, cationic charge transferring compounds, or cationic oxidizing activators, referred to collectively hereinafter as cationic activators. Preferred cationic activators are ammonium, sullonium, phosphonium, oxonium, ferrocenium, silver, lead, carbonium or silylium compounds containing a cation/anion pair that is capable of rendering the Group 3–10 metal complex catalytically active. Preferred anions associated with this cation comprise fluorinated arylborate anions, more preferably, the tetrakis (pentafluorophenyl)borate anion. Additional suitable anions include sterically shielded, bridged diboron anions. Examples of such cationic activators are disclosed in U.S. Pat. No. 5,198,401, 5,132,380, 5,470,927, 5,153,157, 5,350,723, 5,189,192, 5,626,087 and in 5,447,895.

Further suitable activators for activating metal complexes for olefin polymerization include neutral Lewis acids such as tris(perfluorophenyl)borane and tris(perfluorobiphenyl) borane. The former composition has been previously disclosed for the above stated end use in U.S. Pat. No. 5,721,185, and elsewhere, whereas the latter composition is disclosed in Marks, et al, *J. Am. Chem. Soc.* 1996, 118, 12451–12452. Additional teachings of the foregoing activators may be found in Chen, et al, *J. Am. Chem. Soc.* 1997,119, 2582–2583, Jia et al, *Organometallics,* 1997, 16, 842–857 and Coles et al, *J. Am. Chem. Soc.* 1997, 119, 8126–8126.

In U.S. Pat. No. 5,453,410, a strong Lewis acid activator, especially tris-(pentafluorophenyl)borane, was disclosed for use in combination with constrained geometry metal complexes in combination with an alumoxane. This combination beneficially resulted in effective catalyst activation at molar ratios of alumoxane to catalyst that are much lower than required in the absence of the Lewis acid. Suitably, molar ratios from 1:1 to 50:1 could be employed. In U.S. Pat. No. 5,527,929, 5,616,664, 5,470,993, 5,556,928, 5,624,878, the combination of an alumoxane and a strong Lewis acid such as tris-(pentafluorophenyl)boron was disclosed as a suitable activator for use with the metal complexes therein disclosed wherein the metal was in the +2 formal oxidation state. It is known that an exchange reaction between aluminum trialkyl compounds and tris(perfluorophenyl)borane occurs under certain conditions. This phenomenon has been previously described in U.S. Pat. No. 5,602,269.

In U.S. Pat. No. 5,777,120, certain four-coordinate dialkylaluminum amidinate complexes activated with tris (perfluorophenyl)borane were disclosed. The intermediate thought to be formed by the activation was an alumicinium cation derived by Lewis acid abstraction of a methyl group by the borane and stabilized by a Lewis base such as an amine.

It would be desirable to provide activator compositions based on Lewis acids for activation of metal complexes, especially complexes of metals of Group 4 of the Periodic Table of the elements having improved ease of use, cocatalyst properties and efficiency.

SUMMARY OF THE INVENTION

Figure 1:
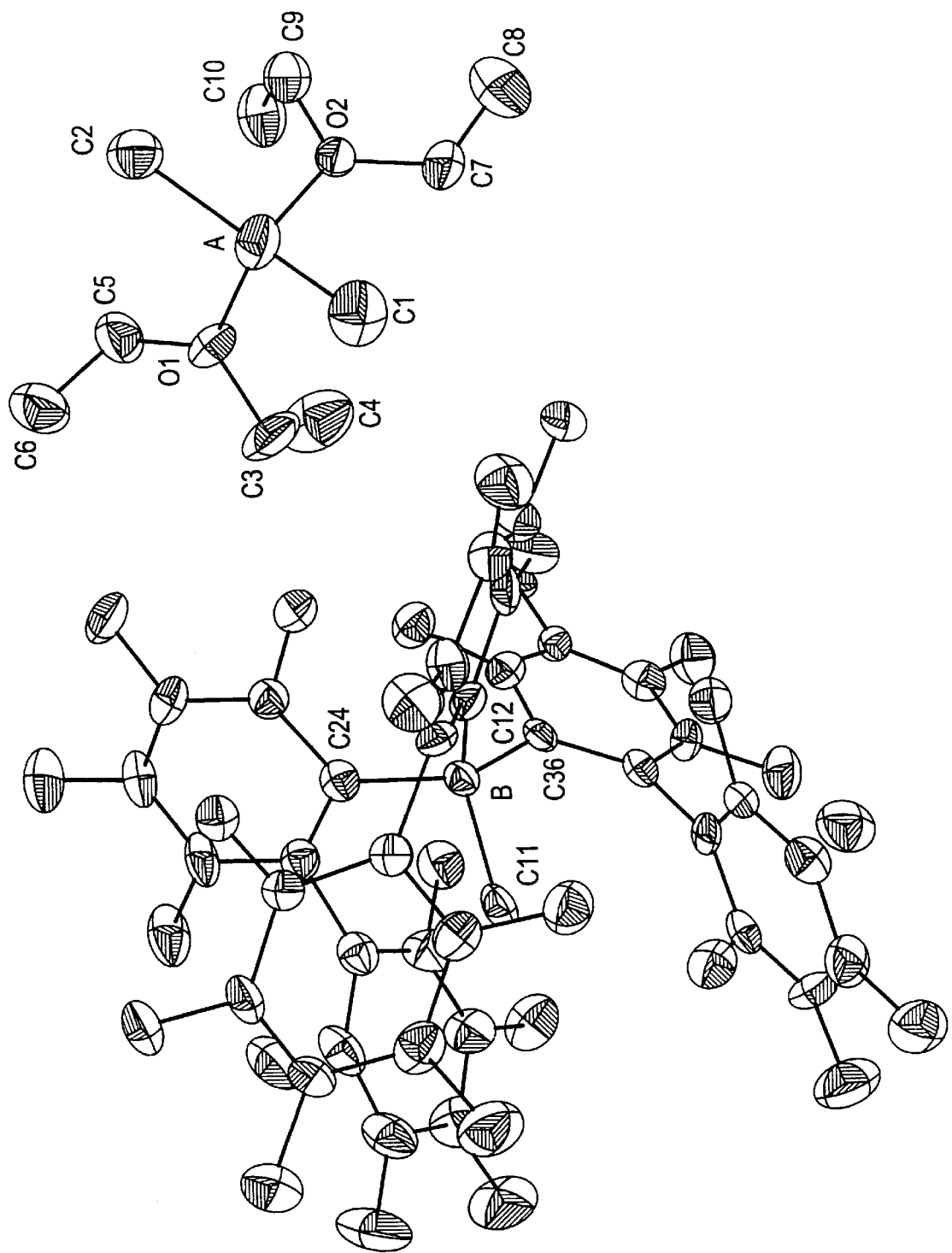
FIG. 1 is the ORTEP structure derived from the single crystal X-ray diffraction data from the product of Example 5.

According to the present invention there is now provided a compound corresponding to the formula:

$$[M'Q^1{}_2L'_{l'}]^+(Ar^f{}_3MQ^2)^-$$

wherein:

M' is aluminum, gallium, or indium.

M is boron, aluminum, gallium or indium $Q^1$ is $C_{1-20}$ hydrocarbyl, optionally substituted with one or more groups which independently each occurrence are hydrocarbyloxy, hydrocarbylsiloxy, hydrocarbylsilylamino, di(hydrocarbylsilyl)amino, hydrocarbylamino, di(hydrocarbyl)amino, di(hydrocarbyl)phosphino, or hydrocarbylsulfido groups having from 1 to 20 atoms other than hydrogen, or, optionally, two or more $Q^1$ groups may be covalently linked with each other to form one or more fused rings or ring systems;

$Q^2$ is an alkyl group, optionally substituted with one or more cycloalkyl or aryl groups, said $Q^2$ having from 1 to 30 carbons;

L' is a monodentate or polydentate Lewis base, preferably L' is reversibly coordinated to the metal complex such that it may be displaced by an olefin monomer, more preferably L' is a monodentate Lewis base;

l' is a number greater than zero indicating the number of Lewis base moieties, L', and $Ar^f$ independently each occurrence is an anionic ligand group; preferably $Ar^f$ is selected from the group consisting of halide, $C_{1-20}$ halohydrocarbyl, and $Q^1$ ligand groups, more preferably $Ar^f$ is a fluorinated hydrocarbyl moiety of from 1 to 30 carbon atoms, most preferably $Ar^f$ is a fluorinated aromatic hydrocarbyl moiety of from 6 to 30 carbon atoms, and most highly preferably $Ar^f$ is a perfluorinated aromatic hydrocarbyl moiety of from 6 to 30 carbon atoms.

The subject invention further provides a process for preparing the foregoing composition, comprising contacting:

(a) a first component corresponding to the formula, $M'Q^1{}_2Q^2$ (b) a second component corresponding to the formula $MAr^f{}_3$, and (c) a Lewis base corresponding to the formula L', wherein M', M, $Q^1$, $Q^2$, $Ar^f$ and L' are as defined above, under conditions to cause transfer of the ligand, $Q^2$.

The subject invention also provides an alternate process for preparing the foregoing composition, comprising contacting:

(a) a first component corresponding to the formula, $M'Q^1{}_2Q^3$ (b) a second component corresponding to the formula $Me^+[MQ^3 Ar^f{}_3]^-$, and (c) a Lewis base corresponding to the formula L', wherein M', M, Q', $Q^2$, $Ar^f$ and L' are as defined above, Me is a metal cation, preferably $Ag^+$, and $Q^3$ is halide, under conditions such that the metal salt, $MeQ^3$, precipitates from the reaction mixture.

The subject invention further provides a catalyst composition useful for polymerization of olefins comprising the above identified cocatalyst composition and a Group 3–10 metal complex.

The compositions surprisingly may alternatively function as olefin polymerization catalysts in the absence of a group 3–10 metal complex. As such, the present invention further includes a catalyst composition comprising a compound corresponding to the foregoing formula in the substantial absence of a Group 3–10 metal complex.

The subject invention further provides a process for polymerization of one or more addition polymerizable monomers comprising contacting the same, optionally in the presence of an inert aliphatic, alicyclic or aromatic hydrocarbon, with the above catalyst compositions.

DETAILED DESCRIPTION

All references herein to elements belonging to a certain Group refer to the Periodic Table of the Elements published and copyrighted by CRC Press, Inc., 1995. Also any reference to the Group or Groups shall be to the Group or Groups as reflected in this Periodic Table of the Elements using the IUPAC system for numbering groups. The full teachings of any patent, patent application, provisional application, or publication referred to herein are hereby incorporated by reference.

Preferred compounds according to the invention are alumicinium tris(fluoroaryl)borates or gallicinium tris (fluoroaryl)borates corresponding to the formula: $[M'Q^1{}_2L'_{l'}]^+(Ar^f{}_3BQ^2)^-$, wherein M' is aluminum or gallium; $Q^1$ is $C_{1-20}$ hydrocarbyl, preferably $C_{1-8}$ alkyl; $Ar^f$ is perfluoroaryl, preferably pentafluorophenyl; and $Q^2$ is $C_{1-8}$ alkyl, preferably $C_{1-8}$ alkyl. More preferably, $Q^1$ and $Q^2$ are identical $C_{1-8}$ alkyl groups, most preferably, methyl, ethyl or octyl.

Preferably the above exchange reaction or salt forming reaction is performed in the presence of excess Lewis base, that is, the reaction preferably is performed in a liquid Lewis base, L'. It has been discovered by the present inventors that the initial exchange product formed upon transfer of a $Q^2$ group remains a cation which is relatively resistant to further ligand exchange. It should be noted however, that the Lewis base originally present in the complex may be further exchanged if desired by contacting the compounds with a different Lewis base. The compositions of the invention are typically hydrolytically unstable and oxygen sensitive and care should be exercised to prevent contact with air or water during preparation or use.

Suitable monodentate Lewis bases include compounds selected from the group consisting of linear or cyclic, aliphatic or aromatic ethers, linear or cyclic, aliphatic or aromatic thioethers, trialkyl amines, triarylamines, trialkylphosphines, triarylphosphines, and mixtures thereof. Examples of polyvalent Lewis bases include linear or cyclic, aliphatic or aromatic polyethers, linear or cyclic, aliphatic or aromatic polyvalent thioethers, aliphatic or aromatic diamines, aliphatic or aromatic triamines, and any compound or polymer containing multiple ether-, thioether-, amine-, or phosphine-functionality. Preferred polydentate Lewis bases include dimethoxyethane, diethoxyethane, dimethoxy-1,3-propane, polyvinylethers, tetramethylethylene diamine (TMEDA), and amine functionalized polymers. The skilled artisan will appreciate that polydentate Lewis bases such as polymeric ether and amine functionalized Lewis bases may also act as solid substrates that convert the present activators to supported polyfunctional activators. Preferred Lewis bases are aliphatic ethers or amines of up to 10 atoms other than hydrogen, more preferably diethyl ether, tetrahydrofuran or ethylene diamine. Generally, when L' is a monodentate Lewis base, l' is 2, when L' is a bidentate Lewis base l' is 1. For polydentate Lewis bases of functionality greater than 2, l' may be less than 1.

The Lewis base may be employed in an excess to that amount required to stabilize the cation formed by the ligand exchange and may also be employed as a solvent. For this reason, diethyl ether and tetrahydrofuran are preferred Lewis bases since they are inexpensive and are easily removed from the product.

The ligand exchange reaction is desirably performed in an aliphatic, cycloaliphatic or aromatic liquid, preferably an alkane of from 5 to 10 carbons, toluene, diethyl ether, tetrahydrofuran or a mixture of the foregoing compounds. The reaction is preferably conducted at a temperature from 0 to 85° C., preferably from 15 to 50° C., most preferably from 20 to 35° C. The exchange reaction is normally conducted for a time from 0.1 seconds to 10 hours, preferably from 1 second to 1 hour, most preferably from 10 seconds to 30 minutes.

The skilled artisan will appreciate that the source of reagents for the foregoing process may include mixtures of first and second compounds, as well as mixtures with other compounds so long as the desired ligand exchange process remains unaffected. In particular, the second compound, which preferably is a trialkylaluminum compound, may be in the form of a mixture with other aluminum compounds, including alumoxanes, which as previously noted may exist as a mixture of oligomeric or cyclic aluminum oxides with trialkyl aluminum compounds.

The present composition is a highly active co-catalyst for use in activation of metal complexes, especially Group 4 metallocenes for the polymerization of olefins. In such use, it is desirably employed as a dilute solution in a hydrocarbon liquid, especially an aliphatic hydrocarbon liquid for use as a homogeneous catalyst, especially for solution polymerizations. Additionally, the composition may be deposited on an inert support, especially a particulated metal oxide or polymer, in combination with the metal complex to be activated according to known techniques for producing supported olefin polymerization catalysts, and thereafter used for gas phase or slurry polymerizations.

When in use as a catalyst activator, the molar ratio of metal complex to activator composition is preferably from 0.1:1 to 3:1, more preferably from 0.2:1 to 2:1, most preferably from 0.25:1 to 1:1, based on the metal content of each component. In most polymerization reactions the molar ratio of metal complex: polymerizable compound employed is from $10^{-12:1}$ to $10^{-1:1}$, more preferably from $10^{-12:1}$ to $10^{-5:1}$.

The reagents employed in the foregoing ligand exchange process, catalyst preparation and use, particularly alumoxane (if present) as well as the support for traditionally supported products, should be thoroughly dried prior to use. The support should preferably be heated at 200–500° C. for a time from 10 minutes to 100 hours prior to use.

The support for the activator component may be any inert, particulate material, but most suitably is a metal oxide or mixture of metal oxides, preferably alumina, silica, an aluminosilicate or clay material. Suitable volume average particle sizes of the support are from 1 to 1000 μM, preferably from 10 to 100 μM. Most desired supports are calcined silica, which may be treated prior to use to reduce surface hydroxyl groups thereon, by reaction with a silane, a trialkylaluminum, or similar reactive compound. Any suitable means for incorporating the alumoxane/tris-(perfluoroaryl)aluminum co-catalyst mixture onto the surface of a support may be used, including dispersing the co-catalyst in a liquid and contacting the same with the support by slurrying, impregnation, spraying, or coating and thereafter removing the liquid, or by combining the cocatalyst and a support material in dry or paste form and intimately contacting the mixture, thereafter forming a dried, particulated product.

Suitable metal complexes for use in combination with the foregoing cocatalysts include any complex of a metal of Groups 3–10 of the Periodic Table of the Elements capable of being activated to polymerize addition polymerizable compounds, especially olefins by the present activators. Examples include Group 10 diimine derivatives corresponding to the formula:

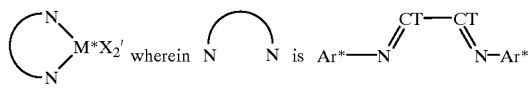

M* is Ni(II) or Pd(II);

X', is halo, hydrocarbyl, or hydrocarbyloxy;

Ar* is an aryl group, especially 2,6-diisopropylphenyl or aniline group; and

CT—CT is 1,2-ethanediyl, 2,3-butanediyl, or form a fused ring system wherein the two T groups together are a 1,8-naphthanediyl group.

Similar complexes to the foregoing are disclosed by M. Brookhart, et al., in *J. Am. Chem. Soc.*, 118, 267–268 (1996) and *J. Am. Chem. Soc.*, 117, 6414–6415 (1995), as being suitable for forming active polymerization catalysts especially for polymerization of α-olefins, either alone or in combination with polar comonomers such as vinyl chloride, alkyl acrylates and alkyl methacrylates.

Additional complexes include derivatives of Group 3, 4, or Lanthanide metals containing from 1 to 3 π-bonded anionic or neutral ligand groups, which may be cyclic or non-cyclic delocalized π-bonded anionic ligand groups. Exemplary of such π-bonded anionic ligand groups are conjugated or nonconjugated, cyclic or non-cyclic dienyl groups, allyl groups, boratabenzene groups, and arene groups. By the term "π-bonded" is meant that the ligand group is bonded to the transition metal by a sharing of electrons from a delocalized π-bond.

Each atom in the delocalized π-bonded group may independently be substituted with a radical selected from the group consisting of hydrogen, halogen, hydrocarbyl, halohydrocarbyl, hydrocarbyloxy, hydrocarbylsulfide, dihydrocarbylamino, and hydrocarbyl-substituted metalloid radicals wherein the metalloid is selected from Group 14 of the Periodic Table of the Elements, and such hydrocarbyl-, halohydrocarbyl-, hydrocarbyloxy-, hydrocarbylsulfide-, dihydrocarbylamino- or hydrocarbyl-substituted metalloid-radicals that are further substituted with a Group 15 or 16 hetero atom containing moiety. Included within the term "hydrocarbyl" are $C_{1-20}$ straight, branched and cyclic alkyl radicals, $C_{6-20}$ aromatic radicals, $C_{7-20}$ alkyl-substituted aromatic radicals, and $C_{7-20}$ aryl-substituted alkyl radicals. In addition two or more such radicals may together form a fused ring system, including partially or fully hydrogenated fused ring systems, or they may form a metallocycle with the metal. Suitable hydrocarbyl-substituted organometalloid radicals include mono-, di- and tri-substituted organometalloid radicals of Group 14 elements wherein each of the hydrocarbyl groups contains from 1 to 20 carbon atoms. Examples of suitable hydrocarbyl-substituted organometalloid radicals include trimethylsilyl, triethylsilyl, ethyldimethylsilyl, methyldiethylsilyl, triphenylgermyl, and trimethylgermyl groups. Examples of Group 15 or 16 hetero atom containing moieties include amine, phosphine, ether or thioether moieties or divalent derivatives thereof, for example amide, phosphide, ether or thioether groups bonded to the transition metal or Lanthanide metal, and bonded to the hydrocarbyl group or to the hydrocarbyl- substituted metalloid containing group.

Examples of suitable anionic, delocalized π-bonded groups include cyclopentadienyl, indenyl, fluorenyl, tetrahydroindenyl, tetrahydrofluorenyl, octahydrofluorenyl, pentadienyl, cyclohexadienyl, dihydroanthracenyl, hexahydroanthracenyl, decahydroanthracenyl groups, and boratabenzene groups, as well as $C_{1-10}$ hydrocarbyl-substituted, $C_{1-10}$ hydrocarbyloxy- substituted, di($C_{1-10}$ hydrocarbyl)amino- substituted, or tri($C_{1-10}$ hydrocarbyl)silyl- substituted derivatives thereof. Preferred anionic delocalized n-bonded groups are cyclopentadienyl, pentamethylcyclopentadienyl, tetramethylcyclopentadienyl, tetramethylsilylcyclo-pentadienyl, indenyl, 2,3-dimethylindenyl, fluorenyl, 2-methylindenyl, 2-methyl-4-phenylindenyl, tetrahydrofluorenyl, octahydrofluorenyl, and tetrahydroindenyl.

The boratabenzenes are anionic ligands which are boron containing analogues to benzene. They are previously known in the art having been described by G. Herberich, et al., in *Organometallics*, 1995, 14, 1, 471–480. Preferred boratabenzenes correspond to the formula:

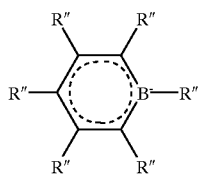

wherein R" is selected from the group consisting of hydrocarbyl, silyl, or germyl, said R" having up to 20 non-hydrogen atoms. In complexes involving divalent derivatives of such delocalized π-bonded groups one atom thereof is bonded by means of a covalent bond or a covalently bonded divalent group to another atom of the complex thereby forming a bridged system.

Suitable metal complexes for use in the catalysts of the present invention may be derivatives of any transition metal including Lanthanides, but preferably of Group 3, 4, or Lanthanide metals which are in the +2, +3, or +4 formal oxidation state meeting the previously mentioned requirements. Preferred compounds include metal complexes (metallocenes) containing from 1 to 3 π-bonded anionic ligand groups, which may be cyclic or noncyclic delocalized π-bonded anionic ligand groups. Exemplary of such π-bonded anionic ligand groups are conjugated or nonconjugated, cyclic or non-cyclic dienyl groups, allyl groups, and arene groups. By the term "π-bonded" is meant that the ligand group is bonded to the transition metal by means of delocalized electrons present in a π bond.

Examples of suitable anionic, delocalized π-bonded groups include cyclopentadienyl, indenyl, fluorenyl, tetrahydroindenyl, tetrahydrofluorenyl, octahydrofluorenyl, pentadienyl, cyclohexadienyl, dihydroanthracenyl, hexahydroanthracenyl, and decahydroanthracenyl groups, as well as $C_{1-10}$ hydrocarbyl-substituted derivatives thereof. Preferred anionic delocalized 7c-bonded groups are cyclopentadienyl, pentamethylcyclopentadienyl, tetramethylcyclopentadienyl, indenyl, 2,3-dimethylindenyl, fluorenyl, 2-methylindenyl and 2-methyl-4-phenylindenyl.

More preferred are metal complexes corresponding to the formula:

$L_lMX_mX'_nX''_p$, or a dimer thereof wherein:

L is an anionic, delocalized, π-bonded group that is bound to M, containing up to 50 atoms not counting hydrogen, optionally two L groups may be joined together through one or more substituents thereby forming a bridged structure, and further optionally one L may be bound to X through one or more substituents of L;

M is a metal of Group 4 of the Periodic Table of the Elements in the +2, +3 or +4 formal oxidation state;

X is an optional, divalent substituent of up to 50 non-hydrogen atoms that together with L forms a metallocycle with M;

X' is an optional neutral Lewis base having up to 20 non-hydrogen atoms;

X" each occurrence is a monovalent, anionic moiety having up to 40 non-hydrogen atoms, optionally, two X" groups may be covalently bound together forming a divalent dianionic moiety having both valences bound to M, or form a neutral, conjugated or nonconjugated diene that is π-bonded to M (whereupon M is in the +2 oxidation state), or further optionally one or more X" and one or more X' groups may be bonded together thereby forming a moiety that is both covalently bound to M and coordinated thereto by means of Lewis base functionality;

l is 1 or 2;

m is 0 or 1;

n is a number from 0 to 3;

p is an integer from 0 to 3; and the sum, l+m+p, is equal to the formal oxidation state of M.

Such preferred complexes include those containing either one or two L groups. The latter complexes include those containing a bridging group linking the two L groups. Preferred bridging groups are those corresponding to the formula $(ER^*_2)_x$ wherein E is silicon or carbon, R* independently each occurrence is hydrogen or a group selected from silyl, hydrocarbyl, hydrocarbyloxy and combinations thereof, said R* having up to 30 carbon or silicon atoms, and x is 1 to 8. Preferably, R* independently each occurrence is methyl, benzyl, tert-butyl or phenyl.

Examples of the foregoing bis(L) containing complexes are compounds corresponding to the formula:

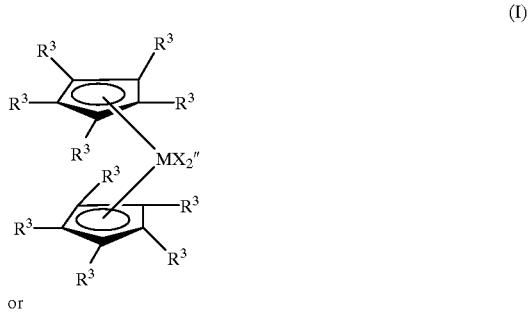

(I)

or

-continued

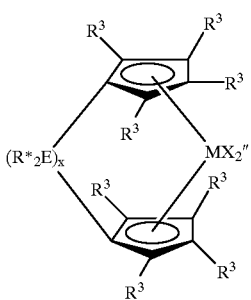

(II)

wherein:
M is titanium, zirconium or hafnium, preferably zirconium or hafnium, in the +2 or +4 formal oxidation state;
$R^3$ in each occurrence independently is selected from the group consisting of hydrogen, hydrocarbyl, dihydrocarbylamino, hydrocarbyleneamino, silyl, germyl, cyano, halo and combinations thereof, said $R^3$ having up to 20 atoms not counting hydrogen, or adjacent $R^3$ groups together form a divalent derivative thereby forming a fused ring system, and
X" independently each occurrence is an anionic ligand group of up to 40 atoms not counting hydrogen, or two X" groups together form a divalent anionic ligand group of up to 40 atoms not counting hydrogen or together are a conjugated diene having from 4 to 30 atoms not counting hydrogen forming a π-complex with M, whereupon M is in the +2 formal oxidation state, and
R*, E and x are as previously defined.

The foregoing metal complexes are especially suited for the preparation of polymers having stereoregular molecular structure. In such capacity it is preferred that the complex possess $C_2$ symmetry or possess a chiral, stereorigid structure. Examples of the first type are compounds possessing different delocalized π-bonded systems, such as one cyclopentadienyl group and one fluorenyl group. Similar systems based on Ti(lV) or Zr(IV) were disclosed for preparation of syndiotactic olefin polymers in Ewen, et al., *J. Am. Chem. Soc.* 110, 6255–6256 (1980). Examples of chiral structures include bis-indenyl complexes. Similar systems based on Ti(IV) or Zr(IV) were disclosed for preparation of isotactic olefin polymers in Wild et al., *J. Orcianomet. Chem*, 232, 233–47, (1982).

Exemplary bridged ligands containing two a-bonded groups are: (dimethylsilyl-bis-cyclopentadienyl), (dimethylsilyl-bis-methylcyclopentadienyl), (dimethylsilyl-bis-ethylcyclopentadienyl, (dimethylsilyl-bis-t-butylcyclopentadienyl), (dimethylsilyl-bis-tetramethylcyclopentadienyl), (dimethylsilyl-bis-indenyl), (dimethylsilyl-bis-tetrahydroindenyl), (dimethylsilyl-bis-fluorenyl), (dimethylsilyl-bis-tetrahydrofluorenyl), (dimethylsilyl-bis-2-methyl-4-phenylindenyl), (dimethylsilyl-bis-2-methylindenyl), (dimethylsilyl-cyclopentadienylluorenyl), (1, 1, 2, 2-tetramethyl-1,2-disilyl-bis-cyclopentadienyl), (1, 2-bis(cyclopentadienyl) ethane, and (isopropylidene-cyclopentadienyl-fluorenyl).

Preferred X" groups are selected from hydride, hydrocarbyl, silyl, germyl, halohydrocarbyl, halosilyl, silylhydrocarbyl and aminohydrocarbyl groups, or two X" groups together form a divalent derivative of a conjugated diene or else together they form a neutral, π-bonded, conjugated diene. Most preferred X", groups are $C_{1-20}$ hydrocarbyl groups.

A further class of metal complexes utilized in the present invention correspond to the formula:

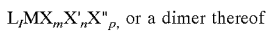

wherein:
L is an anionic, delocalized, π-bonded group that is bound to M, containing up to 50 atoms not counting hydrogen;
M is a metal of Group 4 of the Periodic Table of the Elements in the +2, +3 or +4 formal oxidation state;
X is a divalent substituent of up to 50 non-hydrogen atoms that together with L forms a metallocycle with M;
X' is an optional neutral Lewis base ligand having up to 20 non-hydrogen atoms;
X" each occurrence is a monovalent, anionic moiety having up to 20 non-hydrogen atoms, optionally two X" groups together may form a divalent anionic moiety having both valences bound to M or a neutral $C_{5-30}$ conjugated diene, and further optionally X' and X" may be bonded together thereby forming a moiety that is both covalently bound to M and coordinated thereto by means of Lewis base functionality;
l is 1 or 2;
m is 1;
n is a number from 0 to 3;
p is an integer from 1 to 2; and
the sum, l+m+p, is equal to the formal oxidation state of M.

Preferred divalent X substituents preferably include groups containing up to 30 atoms not counting hydrogen and comprising at least one atom that is oxygen, sulfur, boron or a member of Group 14 of the Periodic Table of the Elements directly attached to the delocalized nbonded group, and a different atom, selected from the group consisting of nitrogen, phosphorus, oxygen or sulfur that is covalently bonded to M.

A preferred class of such Group 4 metal coordination complexes used according to the present invention correspond to the formula:

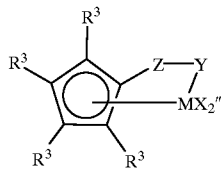

wherein:
M is titanium or zirconium in the +2 or +4 formal oxidation state;
$R^3$ in each occurrence independently is selected from the group consisting of hydrogen, hydrocarbyl, silyl, germyl, cyano, halo and combinations thereof, said $R^3$ having up to 20 non-hydrogen atoms, or adjacent $R^3$ groups together form a divalent derivative (that is, a hydrocarbadiyl, siladiyl or germadiyl group) thereby forming a fused ring system,
each X" is a halo, hydrocarbyl, hydrocarbyloxy or silyl group, said group having up to 20 atoms not counting hydrogen, or two X" groups together form a $C_{5-30}$ conjugated diene;
Y is —O—, —S—, —NR*—, —PR*—; and
Z is SiR*$_2$, CR*$_2$, SiR*$_2$SiR*$_2$, CR*$_2$CR*$_2$, CR*=CR*, CR*$_2$SiR*$_2$, or GeR*$_2$, wherein: R* is as previously defined.

Illustrative Group 4 metal complexes that may be employed in the practice of the present invention include:
cyclopentadienyltitaniumtrimethyl,
cyclopentadienyltitaniumtriethyl,
cyclopentadienyltitaniumtriisopropyl,
cyclopentadienyltitaniumtriphenyl,
cyclopentadienyltitaniumtribenzyl,
cyclopentadienyltitanium-2,4-pentadienyl,
cyclopentadienyltitaniumdimethylmethoxide,
cyclopentadienyltitaniumdimethylchloride,
pentamethylcyclopentadienyltitaniumtrimethyl,
indenyltitaniumtrimethyl,
indenyltitaniumtriethyl,
indenyltitaniumtripropyl,
indenyltitaniumtriphenyl,
tetrahydroindenyltitaniumtribenzyl,
pentamethylcyclopentadienyltitaniumtriisopropyl,
pentamethylcyclopentadienyltitaniumtribenzyl,
pentamethylcyclopentadienyltitaniumdimethylmethoxide,
pentamethylcyclopentadienyltitaniumdimethylchloride,
($\rho^5$-2,4-dimethyl-1,3-pentadienyl)titaniumtrimethyl,
octahydrofluorenyltitaniumtrimethyl,
tetrahydroindenyltitaniumtrimethyl,
tetrahydrofluorenyltitaniumtrimethyl,
(1,1-dimethyl-2,3,4,9,10-$\rho$-1,4,5,6,7,8hexahydronaphthalenyl)titaniumtrimethyl,
(1,1,2,3-tetramethyl-2,3,4,9,10-$\rho$-1,4,5,6,7,8-hexahydronaphthalenyl)titaniumtrimethyl,
(tert-butylamido)(tetramethyl-$\rho^5$-cyclopentadienyl) dimethylsilanetitanium dichloride,
(tert-butylamido)(tetramethyl-$\rho^5$-cyclopentadienyl) dimethyl,
(tert-butylamido)(tetramethyl-$\rho^5$-cyclopentadienyl)-1,2-ethanediylfitanium dimethyl,
(tert-butylamido)(hexamethyl-$\rho^5$-indenyl) dimethylsilanetitanium dimethyl,
(tert-butylamido)(tetramethyl-$\rho^5$-cyclopentadienyl) dimethylsilane titanium (III) 2-(dimethylamino)benzyl;
(tert-butylamido)(tetramethyl-$\rho^5$-cyclopentadienyl) dimethylsilanetitanium (III) allyl,
(tert-butylamido)(tetramethyl-$\eta^5$cyclopentadienyl) dimethylsilanetitanium (II) 1,4-diphenyl-1,3-butadiene,
(tert-butylamido)(2-methylindenyl)dimethylsilanetitanium (II) 1,4-diphenyl-1,3-butadiene,
(tert-butylamido)(2-methylindenyl)dimethylsilanetitanium (IV) 1,3-butadiene,
(tert-butylamido)(2,3-dimethylindenyl) dimethylsilanetitanium (II) 1,4-diphenyl-1,3-butadiene,
(tert-butylamido)(2,3-dimethylindenyl) dimethylsilanetitanium (IV) 1,3-butadiene,
(tert-butylamido)(2,3-dimethylindenyl) dimethylsilanetitanium (II) 1,3-pentadiene,
(tert-butylamido)(2-methylindenyl)dimethylsilanetitanium (II) 1,3-pentadiene,
(tert-butylamido)(2-methylindenyl)dimethylsilanetitanium (IV) dimethyl,
(tert-butylamido)(2-methyl-4-phenylindenyl) dimethylsilanetitanium (II) 1,4-diphenyl-1,3-butadiene,
(tert-butylamido)(tetramethyl-$\eta^5$-cyclopentadienyl) dimethylsilanetitanium (IV) 1,3-butadiene,
(tert-butylamido)(tetramethyl-$\eta^5$-cyclopentadienyl) dimethylsilanetitanium (II) 1,4-dibenzyl-1,3-butadiene,
(tert-butylamido)(tetramethyl-$\eta^5$-cyclopentadienyl) dimethylsilanetitanium (II) 2,4-hexadiene,
(tert-butylamido)(tetramethyl-$\eta^5$-cyclopentadienyl) dimethylsilanetitanium (II) 3-methyl 1,3-pentadiene,
(tert-butylamido)(2,4-dimethyl-1,3-pentadien-2-yl) dimethylsilanetitaniumdimethyl,
(tert-butylamido)(1,1-dimethyl-2,3,4,9,10-$\eta$-4,5,6,7,8-hexahydronaphthalen-4-yl) dimethylsilanetitaniumdimethyl,
(tert-butylamido)(1,1,2,3-tetramethyl-2,3,4,9,10$\eta$-1,4,5,6,7,8-hexahydronaphthalen-4-yl) dimethylsilanetitaniumdimethyl,
(tert-butylamido)(tetramethylcyclopentadienyl) dimethylsilanetitanium 1,3-pentadiene,
(tert-butylamido)(3-(N-pyrrolidinyl)inden-1-yl) dimethylsilanetitanium 1,3-pentadiene,
(tert-butylamido)(2-methyl-s-indacen-1-yl) dimethylsilanetitanium 1,3-pentadiene, and
(tert-butylamido)(3,4-cyclopenta(/)phenanthren-2-y) dimethylsilanetitanium 1,4-diphenyl-1,3-butadiene.

Bis(L) containing complexes including bridged complexes suitable for use in the present invention include:
biscyclopentadienylzirconiumdimethyl,
biscyclopentadienylzirconiumdiethyl,
biscyclopentadienylzirconiumdiisopropyl,
biscyclopentadienylzirconiumdiphenyl,
biscyclopentadienylzirconium dibenzyl,
biscyclopentadienylzirconium-2,4-pentadienyl,
biscyclopentadienylzirconiummethylmethoxide,
biscyclopentadienylzirconiummethylchloride,
bispentamethylcyclopentadienylzirconiumdimethyl,
bisindenylzirconiumdimethyl,
indenylfluorenylzirconiumdiethyl,
bisindenylzirconiummethyl(2-(dimethylamino)benzyl),
bisindenylzirconium methyltrimethylsilyl,
bistetrahydroindenylzirconium methyltrimethylsilyl,
bispentamethylcyclopentadienylzirconiumdiisopropyl,
bispentamethylcyclopentadienylzirconiumdibenzyl,
bispentamethylcyclopentadienylzirconiummethylmethoxide,
bispentamethylcyclopentadienylzirconiummethylchloride,
(dimethylsilyl-bis-cyclopentadienyl)zirconiumdimethyl,
(dimethylsilyl-bis-pentamethylcyclopentadienyl)zirconium-2,4-pentadienyl,
(dimethylsilyl-bis-t-butylcyclopentadienyl) zirconiumdichloride,
(methylene-bis-pentamethylcyclopentadienyl)zirconium (III) 2-(dimethylamino)benzyl,
(dimethylsilyl-bis-indenyl)zirconiumdichloride,
(dimethylsilyi-bis-2-methylindenyl)zirconiumdimethyl,
(dimethylsilyl-bis-2-methyl-4-phenylindenyl) zirconiumdimethyl,
(dimethylsilyl-bis-2-methylindenyl)zirconium-1,4-diphenyl-1,3-butadiene,
(dimethylsilyl-bis-2-methyl-4-phenylindenyl)zirconium (II) 1,4-diphenyl-1,3-butadiene,
(dimethylsilyl-bis-tetrahydroindenyl)zirconium(II) 1,4-diphenyl-1,3-butadiene,
(dimethylsilyl-bis-fluorenyl)zirconiumdichloride,
(dimethylsilyi-bis-tetrahydrofluorenyl)zirconiumdi (trimethylsilyl),
(isopropylidene)(cyclopentadienyl)(fluorenyl) zirconiumdibenzyl, and
(dimethylsilylpentamethylcyclopentadienylfluorenyl) zirconiumdimethyl.

Suitable polymerizable monomers include ethylenically unsaturated monomers, acetylenic compounds, conjugated or non-conjugated dienes, and polyenes. Preferred monomers include olefins, for examples alpha-olefins having from 2 to 20,000, preferably from 2 to 20, more preferably from 2 to 8 carbon atoms and combinations of two or more of such alpha-olefins. Particularly suitable alpha-olefins include, for example, ethylene, propylene, 1-butene, 1-pentene, 4-methylpentene-1, 1-hexene, 1-heptene, 1-octene, 1-nonene, 1-decene, 1-undecene, 1-dodecene, 1-tridecene, 1-tetradecene, 1-pentadecene, or combinations thereof, as well as long chain vinyl terminated oligomeric or polymeric reaction products formed during the polymerization, and $C_{10-30}$ α-olefins specifically added to the reaction mixture in order to produce relatively long chain branches in the resulting polymers. Preferably, the alpha-olefins are ethylene, propene, 1-butene, 4-methyl-pentene-1, 1-hexene, 1-octene, and combinations of ethylene and/or propene with one or more of such other alpha-olefins. Other preferred monomers include styrene, halo or alkyl substituted styrenes, tetrafluoroethylene, vinylcyclobutene, 1,4-hexadiene, dicyclopentadiene, ethylidene norbornene, and 1,7-octadiene. Mixtures of the above-mentioned monomers may also be employed.

In general, the polymerization may be accomplished at conditions well known in the prior art for solution phase, slurry, gas phase and high pressure Ziegler-Natta or Kaminsky-Sinn type polymerization reactions. Examples of such well known polymerization processes are depicted in WO 88/02009, U.S. Pat. Nos. 5,084,534, 5,405,922, 4,588,790, 5,032,652, 4,543,399, 4,564,647, 4,522,987, and elsewhere. Preferred polymerization temperatures are from 0–250° C. Preferred polymerization pressures are from atmospheric to 3000 atmospheres. Molecular weight control agents can be used in combination with the present cocatalysts. Examples of such molecular weight control agents include hydrogen, silanes or other known chain transfer agents. The catalyst composition may be used by itself (homogeneously) or supported on an inert support such as silica, alumina or a polymer.

It is understood that the present invention is operable in the absence of any component which has not been specifically disclosed. The following examples are provided in order to further illustrate the invention and are not to be construed as limiting. Unless stated to the contrary, all parts and percentages are expressed on a weight basis. Where stated, the term "room temperature" refers to a temperature from 20 to 25° C., the term "ovenight" refers to a time from 12 to 18 hours, and the term "mixed alkanes" refers to a mixture of propylene oligomers sold by Exxon Chemicals Inc. under the trade designation Isopar™ E.

EXAMPLES

Tris-(perfluorophenyl)borane (FAB) was obtained as a solid from Boulder Scientific Inc. and used without further purification. Aluminum and gallium reagents were purchased from Strem Chemical Company. and used as received. Modified methylalumoxane (MMAO-3A) in heptane was purchased from Akzo-Nobel. All solvents were purified using the technique disclosed by Pangborn et al, *Organometallics,* 1996, 15, 1518–1520. All compounds and solutions were handled under an inert atmosphere (dry box).

Example 1

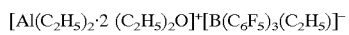

Trispentafluorophenylborane (FAB) (1.00 g, 1.95 mmol) was partly dissolved in 30 mL of diethyl ether. To this mixture 1.95 mL of a 1 M hexane solution of AlEt₃ (1.95 mmol) was added. The resultant reaction mixture was stirred overnight. Solvent was removed under reduced pressure to give 1.502 g of the desired product as a colorless oil in quantitative yield.

Example 2

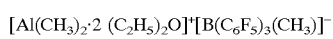

Trispentafluorophenyl borane (FAB) (3.00 g, 5.86 mmol) was partly dissolved in 50 mL of diethyl ether. To this mixture, AlMe₃ (0.422 g, 5.86 mmol) was added in 4 mL of hexane and 2 mL of diethyl ether. During addition of AlMe₃, all the solid dissolved, giving rise to a colorless solution. After stirring for 5 hours at room temperature, solvent was removed under reduced pressure, leaving 4.15 g of the desired product as a colorless oil (97 percent).

Example 3

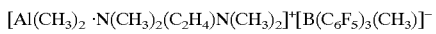

Preparation of

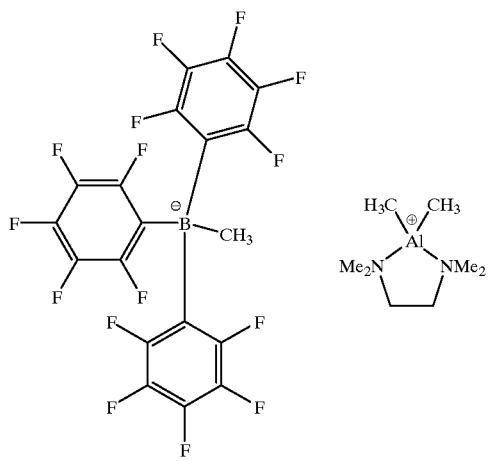

[Me₂Al(OEt₂)₂]⁺[(C₆F₅)₃BMe ](1.00 g, 1.37 mmol from Example 2)—was dissolved in 25 mL of diethyl ether. To this solution 0.159 g (1 37 mmol) of tetramethylethylenediamine was added at room temperature. After stirring for 4 hours at room temperature, 40 mL of hexane was added, causing precipitation of a solid. The flask was put into a freezer overnight at −27° C. After that time, the solid was collected on a frit, washed with hexane and dried under reduced pressure to give 0.86 g (90 percent yield) of the desired prouduct.

Example 4

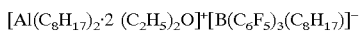

Trispentafluorophenylborane (1.064 g, 2.08 mmol) was partly dissolved in 40 mL of diethyl ether. To this reaction mixture, 3.048 g (2.08 mmol) of Al(Octyl)₃ (25 wt percent in hexane) was added. The resultant reaction mixture was stirred overnight. Solvent was removed under reduced pressure, leaving 2.149 g (quantitative yield) of the desired product as a colorless oil.

Example 5

Preparation of

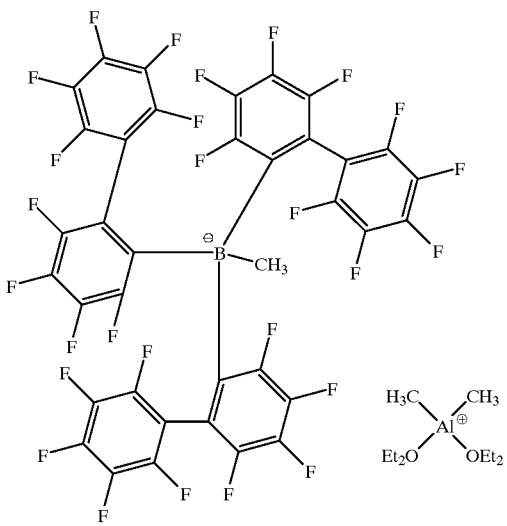

Tris(perfluorobiphenyl)borane diethylether adduct (0.500 g, 0.49 mmol) was dissolved in 20 mL of diethyl ether. To this solution, AlMe$_3$ (0.042 g, 0.58 mmol) was added in 2 mL of diethyl ether. After stirring for 4 hours at room temperature, 40 mL of hexane was added, causing precipitation of a white crystalline solid. After 1 hour, the solvent was decanted and the solid washed with 20 mL of hexane. The hexane wash was decanted, and the solid was dried under reduced pressure to give 0.487 g of the desired product. Yield was 85 percent.

White crystals of the product were obtained by slow precipitation from a toluene/hexane solvent mixture at −27° C. for single crystal X-ray diffraction analysis. Results are shown in FIG. 1.

Example 6

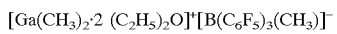

Preparation of

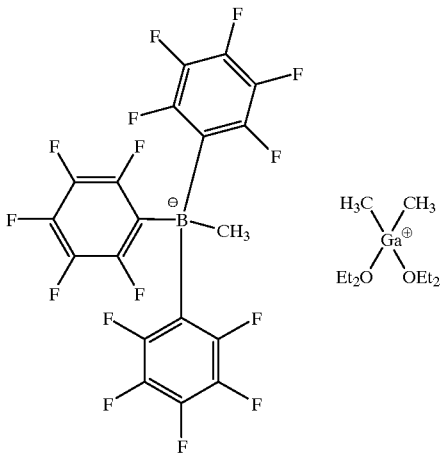

Trispentafluorophenylborane (1.00 g, 1.95 mmol) was dissolved in 20 mL hexane and 20 mL of diethyl ether. To this reaction mixture GaMe$_3$ (0.224 g, 1.95 mmol) was added in 5 mL of ether. During addition, a milky suspension formed. When stirring stopped a colorless oil appeared at the bottom of the flask. After stirring for 5 hours at room temperature, solvent was decanted and the oil washed with 20 mL of hexane. The solvent was decanted again and the oily residue was dried under reduced pressure to give 1.34 g of the desired product. Yield was 88 percent.

Example 7

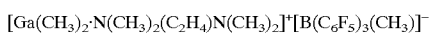

Preparation of

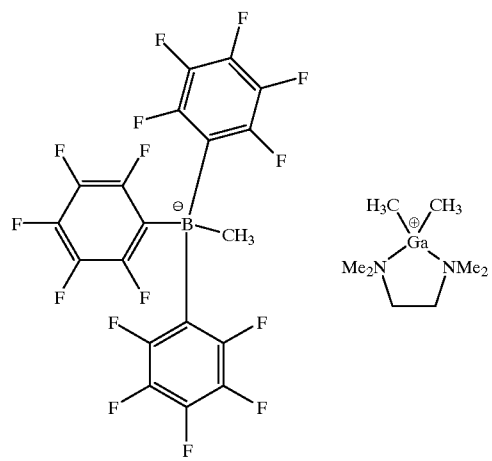

Figure 2:
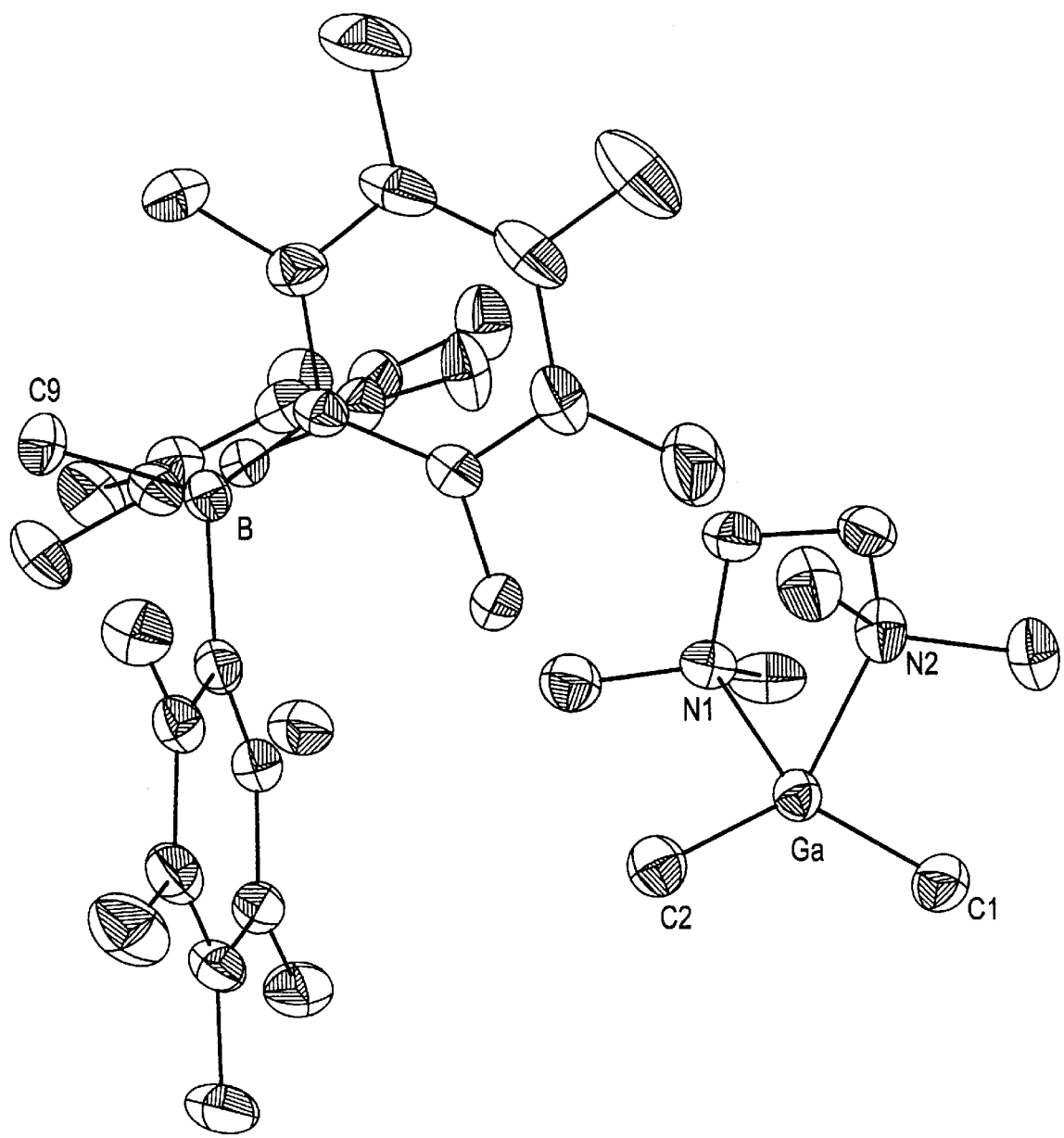
FIG. 2 is the ORTEP structure derived from the single crystal X-ray diffraction data from the product of Example 7.

To 0.5 g (0.65 mmol) of [(C$_6$F$_5$)$_3$BMe][Me$_2$Ga(OEt$_2$)$_2$] from example 6 in 30 mL of Et$_2$O was added 0.075 g (0.65 mmol) of tetramethylethylenediamine. After stirring for 4 hours, the solution was concentrated to 5 mL and then 30 mL of hexane was added causing precipitation of the product as white solid. The solid was collected on a frit, washed with 20 mL of hexane and dried under reduced pressure to give 0.396 g of the desired product. Yield was 83 percent. An ORTEP drawing derived from single crystal X-ray diffraction pattern data is contained in FIG. 2.

Example 8

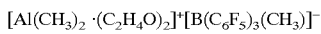

Preparation of

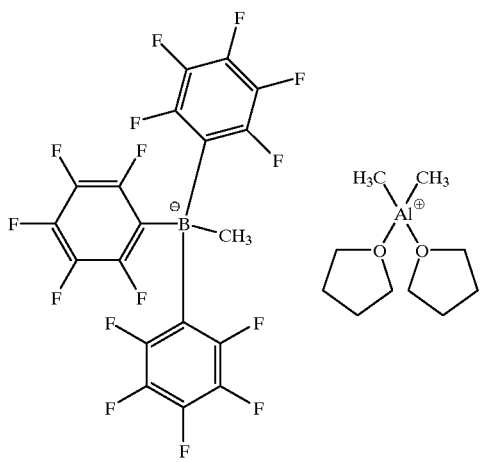

Trispentafluorophenylborane (1.00 g, 1.95 mmol) was partly dissolved in 30 mL of tetrahydrofuran (THF). To this reaction mixture AlMe$_3$ (0.141 g, 1.95 mmol) was added in 4 mL of hexane and 4 mL of THF. After stirring for 0.5 hr. at room temperature, solvent was removed under reduced pressure leaving 1.35 g of the desired product as slightly yellowish oil. Yield was 95 percent Polymerizations All feeds were passed through columns of alumina and a decontaminant (Q-5™ catalyst available from Englehardt Chemicals Inc.) prior to introduction into the reactor. Catalyst and cocatalysts are handled in a glovebox containing an atmosphere of argon or nitrogen.

A stirred 2.0 liter reactor is charged with about 740 g of mixed alkanes solvent and 118 g of 1-octene comonomer. Hydrogen is added as a molecular weight control agent by differential pressure expansion from a 75 ml addition tank at 25 psi (2070 kPa). The reactor is heated to the polymerization temperature of 130° C. and saturated with ethylene at 500 psig (3.4 MPa). Catalyst, ((t-butylamido)(tetramethylcyclopentadienyl)dimethylsilanetitanium 1,3-pentadiene) (Boulder Scientific Inc.), and cocatalyst, as dilute solutions in toluene, are mixed and transferred to a catalyst addition tank and injected into the reactor. The polymerization conditions are maintained for 15 minutes with ethylene added on demand. The resulting solution is removed from the reactor, and 10 ml of a toluene solution containing approximately 67 mg of a hindered phenol antioxidant (Irganox™ 1010 from Ciba Geigy Corporation) and 133 mg of a phosphorus stabilizer (Irgafos™ 168 from Ciba Geigy Corporation) were then added.

Between polymerization runs a wash cycle in which 850 g of mixed alkanes is added to the reactor and the reactor heated to 150° C. The reactor is emptied of the heated solvent immediately before beginning a new polymerization run.

Polymers are recovered by drying in a vacuum oven set at 140° C. for about 20 hours. Density values are derived by determining the polymer's mass when in air and when immersed in methylethyl ketone. Micro melt index values (MMI) are obtained using a "Custom Scientific Instrument Inc. Model CS-127MF-015" apparatus at 190° C. MMI values are unit-less numbers calculated as follows: MMI= 1/(0.00343 t−0.00251), where t= time in seconds. Results are contained in Table 1.

TABLE 1

| Run | activator(s) | μmol catalyst/ activator** | Exotherm (° C.) | Yield (g) | g polymer/ μg Ti | Density (g/ml) | MMI |
|---|---|---|---|---|---|---|---|
| 1 | Ex. 2 | 1.5/3 | 9.1 | 179 | 2.49 | 0.901 | 6.6 |
| A* | FAB/ MMAO-3A | 2/6/20 | 0.8 | 25 | 0.26 | 0.900 | 0.4 |

*comparative example, not an example of the invention
**ratios reflect quantity of metal complex: first activator: second activator (where present)

What is claimed is:

1. A compound corresponding to the formula:

[M'Q$^1_2$L'$_{l'}$]$^+$(Ar$^f_3$MQ$^2$)$^-$ wherein:
M' is aluminum, gallium, or indium;
M is boron, aluminum, gallium or indium;
Q$^1$ is C$_{1-20}$ hydrocarbyl, optionally substituted with one or more groups which independently each occurrence are hydrocarbyloxy, hydrocarbylsiloxy, hydrocarbylsilylamino, di(hydrocarbylsilyl)amino, hydrocarbylamino, di(hydrocarbyl)amino, di(hydrocarbyl)phosphino, or hydrocarbylsulfido groups having from 1 to 20 atoms other than hydrogen, or, optionally, two or more Q$^1$ groups may be covalently linked with each other to form one or more fused rings or ring systems;
Q$^2$ is an alkyl group, optionally substituted with one or more cycloalkyl or aryl groups, said Q$^2$ having from 1 to 30 carbons;
L' is a monodentate or polydentate Lewis base;
l' is a number greater than zero indicating the number of Lewis base moieties, L', and
Ar$^f$ independently each occurrence is a fluorinated aromatic hydrocarbyl moiety of from 6 to 30 carbon atoms.

2. A compound according to claim 1 which is an aluminicinium tris(fluoroaryl)borate or gallicinium tris(fluoroaryl)borate corresponding to the formula: [M'Q$^1_2$L'$_{l'}$]$^+$ (Ar$^f_3$BQ$^2$)$^-$, wherein M' is aluminum or gallium; Q$^1$ is C$_{1-20}$ hydrocarbyl, Ar$^f$ is perfluoroaryl, and Q$^2$ is C$_{1-18}$alkyl.

3. A process for preparing a compound according to claim 1 comprising contacting:
(a) a first component corresponding to the formula, M'Q$^1_2$Q$^2$
(b) a second component corresponding to the formula MAr$^f_3$, and
(c) a Lewis base corresponding to the formula L',
wherein M', M, Q$^1$, Q$^2$, Ar$^f$ and L' are as defined in claim 1, under conditions to cause transfer of the ligand, Q$^2$.

4. A compound according to claim 1 wherein L' is a monodentate Lewis base.

5. A compound according to claim 1 which is:
[Al(C$_2$H$_5$)$_2$·2 (C$_2$H$_5$)$_2$O]$^+$[B(C$_6$F$_5$)$_3$(C$_2$H$_5$)]$^-$,
[Al(CH$_3$)$_2$·2(C$_2$H$_5$)$_2$O]$^+$[B(C$_6$F$_5$)$_3$(CH$_3$)]$^-$,
[Al(CH$_3$)$_2$·N(CH$_3$)$_2$(C$_2$H$_4$)N(CH$_3$)$_2$]$^+$[B(C$_6$F$_5$)$_3$(CH$_3$)]$^-$,
[Al(C$_8$H$_{17}$)$_2$·2 (C$_2$H$_5$)$_2$ O]$^+$[B(C$_6$F$_5$)$_3$(C$_8$H$_{17}$)]$^-$,
[Al(CH$_3$)$_2$·2 (C$_2$H$_5$)$_2$O]$^+$[B(C$_{12}$F$_9$)$_3$(CH$_3$)]$^-$,
[Ga(CH$_3$)$_2$·2 (C$_2$H$_5$ )$_2$O]$^+$[B(C$_6$F$_5$)$_3$(CH$_3$)]$^-$,
[Ga(CH$_3$)$_2$·N(CH$_3$)$_2$(C$_2$H$_4$)N(CH$_3$)$_2$]$^+$8 B(C$_6$F$_5$)$_3$(CH$_3$)]$^-$, or
[Al(CH$_3$)$_2$ ·(C$_2$H$_4$O)$_2$]$^+$[B(C$_6$F$_5$)$_3$(CH$_3$)]$^-$.

* * * * *